United States Patent [19]

Kasser et al.

[11] Patent Number: 5,595,752
[45] Date of Patent: Jan. 21, 1997

[54] INCREASING DRESSING PERCENTAGE AND CARCASS WEIGHT IN FINISHING BEEF CATTLE

[75] Inventors: Thomas R. Kasser, Chesterfield; Jeffrey W. Day, Manchester, both of Mo.

[73] Assignee: Monsanto Company, St. Louis, Mo.

[21] Appl. No.: 269,986

[22] Filed: Jul. 1, 1994

[51] Int. Cl.$^6$ ............................................. A61F 2/00
[52] U.S. Cl. ...................... 424/423; 424/426; 424/438; 514/2; 514/12; 514/21; 604/890.01; 604/891.1
[58] Field of Search ................... 514/2, 12, 21; 424/423, 426, 438; 604/890.01, 891.1

[56] References Cited

U.S. PATENT DOCUMENTS

| | | | |
|---|---|---|---|
| 1,555,711 | 9/1925 | Hershinger | 128/266 |
| 1,642,950 | 9/1927 | Haas | 128/234 |
| 1,929,154 | 10/1933 | Sundock | 128/266 |
| 2,059,966 | 11/1936 | Kaufman et al. | 128/260 |
| 2,086,580 | 7/1937 | Shirley | 128/234 |
| 2,519,555 | 8/1950 | Fields | 128/266 |
| 2,572,155 | 10/1951 | Hoyt | 128/272 |
| 2,587,364 | 2/1952 | Mitchell | 128/217 |
| 3,016,895 | 1/1962 | Sein | 128/217 |
| 3,140,078 | 7/1964 | Krahe et al. | 259/47 |
| 3,141,583 | 7/1964 | Mapel et al. | 222/309 |
| 3,144,178 | 8/1964 | Sarnoff | 222/327 |
| 3,256,884 | 6/1966 | Hill et al. | 128/235 |
| 3,348,545 | 10/1967 | Sarnoff et al. | 128/218 |
| 3,506,008 | 4/1970 | Huck | 128/261 |
| 3,620,216 | 11/1971 | Szymanski | 128/217 |
| 3,760,804 | 9/1973 | Higuchi et al. | 128/260 |
| 4,154,239 | 5/1979 | Turley | 128/217 |
| 4,403,610 | 9/1983 | Lodge et al. | 604/61 |
| 4,452,775 | 6/1984 | Kent | 424/19 |
| 4,492,576 | 1/1985 | Dragan | 433/90 |
| 4,557,724 | 12/1985 | Gregonis et al. | 604/49 |
| 4,576,604 | 3/1986 | Guittard et al. | 604/890 |
| 4,624,847 | 11/1986 | Ayer et al. | 424/15 |
| 4,670,249 | 6/1987 | Ivy | 424/424 |
| 4,721,612 | 1/1988 | Janoff | 424/1.1 |
| 4,723,958 | 2/1988 | Pope et al. | 604/890 |
| 4,725,439 | 2/1988 | Campbell et al. | 424/449 |
| 4,769,011 | 9/1988 | Swaniger | 604/218 |
| 4,786,501 | 11/1988 | Janski | 424/422 |
| 4,787,384 | 11/1988 | Campbell et al. | 128/330 |
| 4,816,439 | 3/1989 | Jorgensen | 514/12 |
| 4,820,267 | 4/1989 | Harman | 604/60 |
| 4,834,268 | 5/1989 | Keller | 222/327 |
| 4,846,793 | 7/1989 | Leonard | 604/62 |
| 4,857,534 | 8/1989 | Croom, Jr. et al. | 514/299 |
| 4,863,736 | 9/1989 | Azain et al. | 424/423 |
| 4,863,901 | 9/1989 | Wilmore | 514/12 |
| 4,891,208 | 1/1990 | Janoff | 424/1.1 |
| 4,917,685 | 4/1990 | Viswanathan et al. | 604/891.1 |
| 4,923,096 | 5/1990 | Ennis, III | 222/391 |
| 4,941,874 | 7/1990 | Sandow et al. | 604/60 |
| 4,959,218 | 9/1990 | Eckenhoff et al. | 424/473 |
| 4,973,304 | 11/1990 | Graham et al. | 604/48 |
| 4,997,825 | 3/1991 | Wagner | 514/171 |
| 5,034,229 | 7/1991 | Magruder et al. | 424/422 |
| 5,035,897 | 7/1991 | Ayer et al. | 424/473 |
| 5,037,420 | 8/1991 | Magruder et al. | 604/892.1 |
| 5,045,082 | 8/1991 | Ayer et al. | 604/892.1 |
| 5,057,318 | 10/1991 | Magruder et al. | 424/438 |
| 5,059,423 | 10/1991 | Magruder et al. | 424/438 |
| 5,091,185 | 2/1992 | Castillo et al. | 424/438 |
| 5,100,392 | 3/1992 | Orth et al. | 604/175 |
| 5,110,596 | 5/1992 | Magruder et al. | 424/438 |
| 5,112,614 | 5/1992 | Magruder et al. | 424/422 |
| 5,135,523 | 8/1992 | Magruder et al. | 604/892 |
| 5,137,727 | 8/1992 | Eckenhoff | 424/422 |
| 5,156,851 | 10/1992 | Castillo et al. | 424/497 |
| 5,162,116 | 11/1992 | Shepherd | 424/438 |
| 5,174,999 | 12/1992 | Magruder et al. | 424/423 |
| 5,180,591 | 1/1993 | Magruder et al. | 424/473 |
| 5,209,746 | 5/1993 | Balaban et al. | 604/892 |
| 5,219,572 | 6/1993 | Sivaramakrishnan et al. | 424/438 |
| 5,223,266 | 6/1993 | Eckenhoff et al. | 424/473 |
| 5,227,167 | 7/1993 | Carr et al. | 424/438 |
| 5,232,708 | 8/1993 | Castillo et al. | 424/497 |
| 5,234,692 | 8/1993 | Magruder et al. | 424/473 |
| 5,234,693 | 8/1993 | Magruder et al. | 424/473 |
| 5,234,694 | 8/1993 | Magruder et al. | 424/473 |
| 5,238,687 | 8/1993 | Magruder et al. | 424/473 |
| 5,281,197 | 1/1994 | Arias et al. | 604/57 |
| 5,292,307 | 3/1994 | Dolzine et al. | 604/54 |
| 5,304,119 | 4/1994 | Balaban et al. | 604/51 |
| 5,312,333 | 5/1994 | Churinetz et al. | 604/57 |
| 5,329,616 | 6/1994 | Magruder et al. | 604/892.1 |

FOREIGN PATENT DOCUMENTS

| | | | |
|---|---|---|---|
| 59922 | 12/1987 | Australia | A61K 37/36 |
| 333349 | 9/1989 | European Pat. Off. | A61K 31/135 |
| 0374120 | 6/1990 | European Pat. Off. | A61K 47/10 |
| 8901281 | 7/1991 | Netherlands | A61D 7/00 |
| 70343 | 10/1970 | South Africa . | |
| WO92/00728 | 1/1992 | WIPO | A61K 9/22 |
| WO92/16194 | 10/1992 | WIPO | A61K 9/22 |
| WO94/04187 | 3/1994 | WIPO | A61K 39/00 |
| WO94/04183 | 3/1994 | WIPO | A61K 37/36 |

OTHER PUBLICATIONS

McBride and Mosely, "Influence of Exogenous Somatotropin on the components of Growth in Ruminants", The Technologies, 91–95.

Early et al., "Growth Feed Efficiency and carcass characteristics of beef steers treated with daily injections of recombinantly–derived bovine somatotropin", Abstract (1988).

Wagner et al., "Effect of growth hormone (GH) and estradiol ($E_2\beta$) alone and in combination on beef steer growth performance, carcass and plasma constituents", Abstract (1988).

T. R. Kasser, Presentation, Continuous Intraperitoneal bST Delivery and Improved Performance in Feedlot Steers Also Treated With Steroids, Tylosin, and Monensin, American Society of Animal Science Meeting, Jul. 6–9, 1993.

(List continued on next page.)

Primary Examiner—Frederick Krass
Attorney, Agent, or Firm—George R. Beck; Gary M. Bond

[57] ABSTRACT

Beef cattle treated with bovine somatotropin and an estrogenic agent during the final stages of growth show improved carcass weight and dressing percent when the somatotropin is administered intraperitoneally at a substantially constant rate.

14 Claims, No Drawings

OTHER PUBLICATIONS

T. R. Kasser, et al., Continuous intraperitoneal bST delivery and improved performance in feedlot steers also treatd with steroids. Abstract, American Society of Animal Science.

W. J. Enright, et al., Effects of long-term administration of pituitary-derived bovine growth hormone and estradiol on growth in steers. Abstract, J. Anim. Sci 1990 vol. 68: 2345–2356.

R. L. Preston, et al., Comparative effects of BST and steroidal growth promotants in feedlot steers. Abstract 71, J. Animal Science 67, Suppl. 1: 215, 1989.

R. L. Preston, et al., Role of protein level and source on the response of feedlot steers to levels of somatotropin. Abstract 173, . . .

J. Fabry et al., Influence de l'hormone de croissance sur la production de viande chez les genisses. Abstract, . . .

R. J. Early, et al., Growth, feed efficiency and carcass characterirstics of beef steers treated with daily injections of recombinantly-derived bovine somatotropin. Abstract 158, .

J. F. Wagner, et al., Effect of growth hormone (GH) and estradiol ($E_2\beta$) alone and in combination on beef steer growth performance, carcassand plasma constituents. Abstract 159, . . .

R. L. Preston, et al, Comparative effectiveness of somatotropin and anabolic steroids in feedlot steers. Abstract . . .

W. M. Moseley, et al., Recombinant bovine somatotropin improves growth performance in finishing beef steers. J. Animal Science 1992 70:412–425, Abstract . . .

R. J. Early, et al., Growth and metabolism in somatotropin-treated steers. J. Animal Science 1990 68:4134–4143, Abstract . . .

B. W. McBride, et al., Influence of exogenous somatotropin on the components of growth in ruminants. Abstract, . . .

T. R. Kasser, et al., Effect of weekly BST Pellet implanttion on growth, feed efficienty and lean yield of feedlot steers. Abstract 5362 . . .

T. R. Kasser, et al., Mode and site of delivery of the effectiveness of somatotropin (ST) on growth in nature female rats. Abstract 4137 . . .

D. L. Hancock, et al., Titration of the recombinant bovine somatotropin dosage that maximizes the anabolic response in feedlot steers. J. Animal Science 1990 68: 4117–4121, Abstract . . .

P. P. Groenewegen, et al., Effect of bovine somatotropin on the growth rate, hormone profiles and carcass composition of holstein bull calves. Domestic Animal Endocrinology, vol. 7(1):43–54, 1990, Abstract . . .

E. P. Stanisiewski, et al., Milk Yield, health, and Reproduction of dairy cows given somatotropin (somavubove) beginning early postpartum. J. Dairy Science 1992 75: 2149–2164, Abstract . . .

R. J. Early, et al., Growth and metabolism in somatotropin-treated steers: II. Carcass and noncarcass tissue components and chemical composition. J. Animal Science 1990 68:4144–4152, Abstract . . .

R. J. Early, et al., Growth and metabolism in somatotropin-treated steers: III Protein synthesis and tissue energy expenditures. J. Animal Science 1990 68: 4153–4166, Abstract . . .

Colin J. Peel, et al., Effect of exogenous growth hormone on lactational performance in high yielding dairy cows. J. Nutr. 111: 1662–1671, 1981, Abstract . . .

L. D. Sandles, et al, Growth and carcass composition of pre-pubertal dairy heifers trated with bovine growth hormone. Animal Prod. 1987 44: 21–27 Abstract . . .

T. S. Rumsey, et al., Growth response to an estrogenic growth promoter and recombinant bovine somatotropin (BST) in young beef steers. Abstract 917 . . .

B. H. Breier, et al., Influence of nutritional status and oestradiol-17β on plasma growth hormone, insulin-like growth factors-I and -II and the response to exogenous growth hormone in young steers. J. Endocr. (1988) 118, 243–250, Abstract . . .

J. F. Roche et al., The effects of steroid hormones and xenobiotics on growth of farm animals. Abstract . . .

B. H. Breier, et al., The somatotrophic axis in young steers: influence of nutritional status and oestradiol-17β on hepatic high-and low-affinity somatotrophic binding sites. J. Endocr. (1988) 116, 160–177, Abstract . . .

E. L. Potter, et al., The effect of feed additives and anabolic implants upon the feed intake of beef cattle. Abstract . . .

Y. W. Chien, Novel drug delivery systems. Abstract . . .

C. A. Baile et al., The bST delivery profile and efficiacy in holstein heifers receiving intraperitoneal 84-day sustained delivery systems. Abstract . . .

J. F. Wagener et al., The effect of bovine growth hormone (bGH) and estradiol ($E_2\beta$) alone and in combination on urinary nitrogen excretion in beef steers. Abstract 90 . . .

Endopath Tristar Trocar Package Graphics 1993.

Endopath Tristar Trocar Advertising Mailer 1992.

Proceedings, Scientific Seminar on Development in Korea, Efficacy and Safety of Bovine Somatotropin in Holstein and Hanwoo pp. 1, 70–88, May 24, 1994.

INCREASING DRESSING PERCENTAGE AND CARCASS WEIGHT IN FINISHING BEEF CATTLE

FIELD OF THE INVENTION

The invention relates to the treatment of beef cattle during the finishing stage of growth. In a particular aspect the invention relates to treating beef cattle during the finishing stage of growth in a feed lot to increase weight gain and to increase the proportion of weight gain which appears in carcass components, significantly increasing both dressing percentage and carcass weight.

BACKGROUND OF THE INVENTION

Bovine somatotropin (bST), usually in the form of recombinant bST (rbST), is a broad-acting polypeptide hormone which influences a wide range of complex functions in cattle, including growth rate, maturation, milk production and the like.

Studies on the use of bST in finishing beef cattle to provide commercially advantageous methods of preparing beef cattle for slaughter have successfully increased the average daily gain and slaughter weight of the cattle. However, bST treatment typically decreases the dressing percentage of the cattle.

When cattle are slaughtered, the body weight consists of carcass weight, non-carcass body components, and digestive fill. The carcass weight is the weight of the carcass, including the kidneys, but not including the head, hide, hooves, viscera including digestive fill, and other internal organs. The ratio of the carcass weight of the animal to the total body weight in percent is referred to as the dressing percentage.

bST administration to beef cattle during the finishing stage of growth has also been found, when continued substantially until slaughter, to increase the proportion of weight gain which appears in non-carcass components. This calculation can frequently be made from data presented in the prior art references. Thus, bST-induced increase in body weight has typically been disproportionately allocated to commercially less-valuable non-carcass components of the animals.

When cattle are being prepared for slaughter, it would be advantageous to increase significantly both the dressing percentage and the carcass weight, since in this way the investment in feed supplementation and treatment during the finishing stage would reduce cost per unit of meat. Heretofore, there has been no reliable method of significantly increasing the dressing percentage of cattle receiving bST and preferentially allocating the increase in body weight to the more valuable carcass components.

Fabry et al., "Influence de l'hormone de croissance sur la production de viande chez les genisses," Reprod. Nutr. Develop. Vol. 27 (2B) 591–600 (1987) showed that the dressing percent value in heifers of the Belgian White Blue breed injected daily with about 50 milligram/day (mg/d) of bST dropped from 58.9% to 57.9%. Only about 36% of the weight increase in the bST-treated heifers appeared in the carcass components.

Early et al., "Growth and Metabolism in Somatotropin-treated Steers: I. Growth, Serum Chemistry and Carcass Weights," J. Anim. Sci. 68:4134–4143 (1990) showed that the dressing percent value in Hereford steers daily injected with about 20 mg/d of bST dropped from 53.8% to 51.8%. Early et al., "Growth and Metabolism in Somatotropin-treated Steers: II. Carcass and Noncarcass Components and Chemical Composition," J. Anim. Sci. 68:4144–4152 (1990) showed that most of the body weight gain in such steers was in the non-carcass components. Only about 12% of the weight increase in the bST-treated steers appeared in the carcass components.

Mosely et al., "Recombinant Bovine Somatotropin Improves Growth Performance in Finishing Beef Steers," J. Anim. Sci. 70:412–425 (1992) showed in two experiments that increasing dosage of bST administered by daily injection to cross-bred steers in the finishing stage of growth, while increasing feed efficiency ("FE") and average daily gain ("ADG"), decreased dressing percentage. In a first experiment, dosages of rbST of 33 and 100 ug/kg decreased dressing percentage from 62.7 to 61.3% and a dosage of 300 ug/kg decreased dressing percentage from 62.7 to 58.7%. In a second experiment, treatment with rbST at 8.25, 16.5, or 33 ug/kg decreased dressing percentage from 63.2 to 62.5 or 62.6% while treatment with 66 ug/kg rbST reduced dressing percentage from 63.2 to 61.9%. The cattle were slaughtered at constant weight. These studies suggested that as average daily bST dose increased, the extent to which dressing percent was diminished also increased.

Wagner et al., "Effect of growth hormone (GH) and estradiol ($E_2\beta$) alone and in combination on beef steer growth performance, carcass and plasma components," showed that subcutaneous injections of a biweekly-administered oil formulation containing 960 mg bST to cross-bred beef steers decreased dressing percent from 63.0% to 61.1%. In combination with estradiol, rbST treatment decreased dressing percentage from 64 to 61.4%. The biweekly bST treatment, in the presence or absence of estradiol, resulted in all of the weight increase being allocated to the non-carcass components.

In Enright et al., Effects of long term administration of pituitary-derived bovine growth and estradiol on Friesian steers, J. Anim. Sci. 68: 2345–2356 (1990), daily injections of bST were discontinued at 22 weeks whereas estradiol treatment was continued until slaughter at 30 weeks. Carcass analysis was not obtained at the end of bST administration, but was conducted eight weeks after the last bST injection. Sandles et al., Anim. Prod. 44:21–27 (1987) had shown that bST effects were lost about 5 weeks after cessation of bST injection. Thus, carcass data obtained eight weeks post bST injection may not be valid for examining bST dressing percentage responses. bST administration to the finishing stage cattle ending eight weeks prior to slaughter generally had no significant effect on carcass weight and had no significant effect on dressing percentage.

Preston et al., "Comparative effects of BST and steroidal growth promotants in feedlot steers," American Society of Animal Science, American Dairy Science Association, Midwest Section, Mar. 23–25, 1992, reported that when bST was administered by intraperitoneal sustained release pellets (first-order release) dressing percent was not significantly changed. See, also, Preston et al., "Role of protein level and source on the response of feedlot steers to levels of somatotropin," Journal of Animal Science, Volume 71, Supplement 1, Abstract 173.

Rumsey et al., Growth Response to an estrogenic growth promoter and recombinant bovine somatotropin (bST) in young beef steers, FASEB 1994 pA158, Abstract Number 917 reported results of treating young cross-bred steers with bST, estrogen, and a combination of bST and estrogen. Rumsey et al. did not report dressing percentage, but provided data from which the dressing percentage for the various treatments could be estimated. These data indicated that treatment with estradiol increased dressing percent (56%), that bST treatment decreased dressing percent (53%) and that concurrent treatment with bST and estrogen/progesterone resulted in no change in dressing percent (54%), all relative to controls (54%).

In McBride and Mosely, Influence of Exogenous Somatotropin on the Components of Growth in Ruminants, the authors summarize the work on bST in cattle and sheep: Body weight gain is often accompanied by an increase in non-carcass components and the carcass weight may not be significantly increased.

Thus, summarizing these articles, while estrogen alone had been observed to increase dressing percentage in cattle not being treated with bST, there remains a need for an effective treatment which includes administration of bST and which will significantly increase both dressing percentage and carcass weight of cattle in the finishing stage of growth.

These and other advantages can be achieved by those skilled in the art in accordance with the invention herein disclosed. The invention is not limited to the embodiments specifically disclosed herein, but by the claims attached hereto interpreted in accordance with law.

SUMMARY OF THE INVENTION

It has been discovered that treatment of cattle in the finishing stage of growth with intraperitoneally released bST, concurrent with treatment by an estrogenic agent, increases the proportion of gained weight which appears in the carcass components. That is, treatment of beef cattle in the finishing stage of growth in accordance with the invention increases the relative proportion of weight of the carcass components and decreases the relative proportion of weight of the non-carcass components.

The invention comprises a method of preparing beef cattle for slaughter. A source of bST is implanted in the intraperitoneal space of beef cattle in the finishing stage of growth being prepared for slaughter. bST is released in the intraperitoneal space at a rate and a dose effective for increasing the body weight (BW) or feed conversion efficiency (FE) or carcass weight (CW) or average daily gain (ADG) of beef cattle in the finishing stage of growth over an extended period of time ending substantially at slaughter of the animals. Concurrently, the animals are treated subcutaneously or intraperitoneally with an estrogenic agent at a dose effective for increasing the body or carcass weight (BW or CW) of beef cattle in the finishing stage of growth. The dressing percentage and carcass weight of the bST- and estrogenic agent-treated animals are significantly increased.

DETAILED DESCRIPTION OF THE INVENTION

The invention relates to a method of preparing beef cattle in the finishing stage of growth for slaughter. The finishing stage of growth is the final stage of growth before slaughter, and follows the stocker stage of growth when the bovine receives nutrients primarily from pasturage or hay, optionally with feed supplementation, which in turn follows the calf or suckling stage when the calf receives nutrients primarily from its mother.

Cattle in the finishing stage of growth are generally nonlactating bovines (steers or heifers) of 12 months (or even as low as 3 months) to 2 years of age who are undergoing rapid growth. The finishing stage of growth can be regarded as beginning when the typical beef stocker is about 700 pounds (about 320 kg) of weight. Such animals will usually be slaughtered when a weight of about 1000 or 1300 pounds (about 450 kg or 600 kg) or more is reached.

The finishing stage of growth is a period of time during growth when the bovine is of sufficient size and age when supplied with a suitable feed to undergo a rapid average daily weight gain, for example, an average daily gain of at least 1 kg/d, that is, when the rate of weight gain is 1 or more than 1 kg/d. Typically, cattle during this phase of growth can gain in the range of about 1 to about 2 kilograms or even more per day. Preferably, the cattle treated in accordance with the invention are high-performance cattle capable of growth at a rate of greater than about 1.5 kg/d, most preferably at a rate greater than about 1.7 kg/d. The current limit of average daily gain (ADG) during finishing is about 3 kg/d; however, as higher performance cattle are developed, this limit may be exceeded. In any case, the range above 1 or 1.5 etc. kg/d is finite and definite and will be known to those skilled in the art.

During the finishing stage of growth, the bovine feed may be supplemented with concentrated feed, richer than pasturage or hay in digestible proteins, carbohydrates, and fats. Typically, during the finishing stages, feed grain may constitute from 12 to 80% or more of the animal's feed. The feed may contain from 12 to 16 percent or more protein or protein-equivalent nitrogen. National Research Council. (NRC) guidelines permit finishing at as low as 9% protein-equivalent nitrogen.

It has been found that feed efficiency, body and carcass weight and dressing percent are advantageously influenced when beef cattle receiving an estrogenic agent are treated intraperitoneally with an effective dose and rate of release of bST during this period of growth.

bST (bovine somatotropin) refers to any protein having bovine somatotropin activity. The bovine somatotropin can be pituitary-derived or recombinantly produced bovine somatotropin. The bST can be a naturally-occurring sequence or a sequence altered by addition or deletion or substitution of one or more amino acids. All of these forms of bovine somatotropin are now well-known to those skilled in the art.

Examples of bovine somatotropin variants include, but are not limited to, polypeptides having the following amino acid sequences with unspecified amino acid residues being the same as or similar to the naturally occurring somatotropin:

$NH_2$-met-phe(1)-pro(2) . . . leu(126) . . . phe(190)-COOH
$NH_2$-met-phe(1)-pro(2) . . . val(126) . . . phe(190)-COOH
$NH_2$-ala-phe(1)-pro(2) . . . val(126) . . . phe(190)-COOH
$NH_2$-ala-phe(1)-pro(2) . . . leu(126) . . . phe(190)-COOH
$NH_2$-phe(1)-pro(2) . . . leu(126) . . . phe(190)-COOH
$NH_2$-phe(1)-pro(2) . . . val(126) . . . phe(190)-COOH
$NH_2$-met-asp-glu-phe(1)-pro(2) . . . leu(126) . . . phe(190)-COOH
$NH_2$-met-asp-glu-phe(1)-pro(2) . . . val(126) . . . phe(190)-COOH
$NH_2$-met(4)-ser(5) . . . leu(126) . . . phe(190)-COOH
$NH_2$-met(4)-ser(5) . . . val(126) . . . phe(190)-COOH
$NH_2$-met-phe(10) . . . leu(126) . . . phe(190)-COOH
$NH_2$-met-phe(10) . . . val(126) . . . phe(190)-COOH The first variant in the list above, with a methionyl residue at the N-terminus, and a leucyl residue at position 126 may be specifically referred to as methionyl bovine somatotropin or "MBS", and the third variant in the list above, with an alanyl residue at the N-terminus and a valyl residue at position 126 may be referred to as alanyl-valyl bovine somatotropin or "alaval BST" or "A-BST". Metal complexes of such bST, such as zinc and copper complexes, may also be used and are referred to as Zn-bST or Cu-bST. See, e.g., U.S. Pat. No. 4,863,736.

It is understood that the additional N-terminal methionyl residue on the variants described above could also be removed, either during or after expression. It is also understood that one or more amino acids of the following sequence -glu-arg-ala-tyr-ile-pro-glu- (which are numbers 32–38 of the bovine somatotropin sequence set forth above) may be deleted. This type of deletion is described in European Patent Application, Publication Numbers 282,318, and 282,319, both of which were published Sep. 14, 1988. Other deletion variants with somatotropin activity can also be used, such as deletion of amino acids 32–45.

The somatotropins found most effective for administration via the composition of the invention are those which have an N-terminal group of methionine and are associated with zinc metal. See, e.g., U.S. Pat. No. 4,985,404, incorporated herein by reference.

The formulation of bovine somatotropin for use in an osmotic implant may generally include a stabilizing polyol. The phrase "stabilizing polyol" means polyol, for example, with three hydroxyl groups, which maintains the somatotropin in a physically stable composition, i.e. the somatotropin does not precipitate to an undesirable degree over reasonable storage or administration period. Glycerol is the preferred polyol, however, other polyols may be used, such as tris(hydroxymethyl)aminomethane.

The formulation may further include a physiologically compatible buffer, incorporated for maintaining the pH exhibited by the composition within a range in which the somatotropin is bioactive. Generally, the pH exhibited by the solution should be between a minimum of about 4.5 or, preferably about 5, or more preferably 5.7 and a maximum of the greater of about 7 and about the isoelectric point of the somatotropin. The isoelectric point for A-BST is 8.6. These isoelectric points are for the standard monomeric forms obtained in bulk preparation of these somatotropins. Isoelectric points for other variants, other derivatives and other forms can be determined using standard techniques. For A-BST, the optimum pH is about between about 6.1 and about 7.5. Although various buffers can be used, it is preferred that the buffer be an alkali metal phosphate. To provide buffering in the desired pH range, it is particularly preferable that the buffer be comprised substantially of monobasic:dibasic phosphates such as, for example, mono- or-di-sodium or potassium phosphates at 1M or 0.45M or the like. Another effective buffer for controlling the pH in the desired range is a histidine hydrohalide such as histidine hydrochloride. Additional buffers that maintain this pH range are citrate buffers and acid addition salts of tris(hydroxymethyl)aminomethane, such as the hydrochloride salt. These tris(hydroxymethyl)aminomethane salts also contain hydroxyl groups and can act as a stabilizing polyol in some circumstances. Any other buffer that can maintain a pH in the desired range can be used.

It should incidentally be noted that direct measurement of the pH of the composition of the invention may not in all instances be practical. To provide a practical measurement, however, a small quantity such as a drop of the composition may be placed in about 10 ml of water, and the pH of the resulting mixture determined. It is believed that the actual pH of the composition is closely approximated by this measurement, but, in any event, it will be understood that the pH measured at such dilution is considered for purposes of this disclosure to be the pH exhibited by the composition itself.

In order to promote wetting of the somatotropin by the buffer/polyol excipient during preparation of the formulation, a wetting agent, such as a nonionic surfactant is preferably incorporated as well. Such surfactant also inhibits foaming. The surfactant can be present in the excipient at amounts between about 0.05% and about 2.5% more preferably about 0.25%. A particularly preferred nonionic surfactant is a polyethoxylated sorbitan ester, such as a tri(polyoxyethylene) ester of sorbitan mono-oleate, such as that sold under the trade designation Tween 80 by ICI Americas Inc.

An advantage of the use of a buffered polyol excipient for the somatotropin is the high loading achievable due to the high solubility of the somatotropin in the excipient liquid. Despite the high concentration of somatotropin in a composition which also contains a significant fraction of water, the pH maintained by the buffer inhibits the formation of dimers and other aggregates. Although it has not been determined whether the somatotropin is true solution or colloidal solution, it is desirable that the somatotropin does not precipitate or otherwise separate from the excipient, either on standing or under the influence of shear encountered in passage of the composition through the discharge opening of an infusion pump. The concentration of somatotropin in the composition is at least about 10% by weight, preferably at least about 15% by weight, more preferably at least about 20% by weight and even more preferably at least about 25% or even about 30% by weight. The somatotropin concentration may range as high as about 45% by weight. The polyol concentration may be at least about 20% by weight or 25% by weight and may range as high as 80% by weight or 70% by weight or 60% by weight or 50% by weight or 40% by weight. A relatively high glycerol content additionally provides a bacteriostatic effect. It is generally considered that an excipient containing about 50% glycerol provides bacteriostatic effect. The osmotic implant may further contain an estrogenic agent, for example, 17-β-estradiol, at a concentration of about 0.05 to about 1%, more preferably about 0.18 to about 0.72%.

Preferably, the formulation further comprises a wetting agent, such as nonionic surfactant with optimum concentrations between about 0.005% or about 2.5% by weight. Except for the buffer salt, which in the case of a phosphate buffer may typically comprise 4% to 7% by weight, and the sodium or potassium chloride which may be added to stabilize the formulation, described below, the balance of the formulation typically is water. A preferred formulation contains at least about 7% water, more preferably at least about 15% water, and even more preferably between about 25% and about 35% by weight water.

Optionally an alkaline halide such as sodium chloride or potassium chloride is added to the excipient prior to formulation with somatotropin. It has been found that this facilitates maintaining homogeneity of the formulation during filling of the implants, for example, when using Zn-bST. Following addition of the somatotropin to the excipient, the filled implant can be subjected to heat treatments from about 6 to 24 hours, preferably 16 hours, at a temperature between about 35° C. and 50° C., preferably 39°–46° C., most preferably about 40° C. Preferably the alkaline chloride comprises about 1 to about 4% by weight of the final formulation.

The formulation is normally a clear, homogeneous single phase. The formulation appears as a solid or semisolid at typical storage temperatures of about 4° C. The formulation decreases in viscosity to produce a viscous liquid at the body temperature of an animal. In this way, the formulation can be dispensable without being readily fluid at all temperatures.

As the concentration of somatotropin rises above 25%, the ratios of water and buffer to somatotropin preferably decline with increasing somatotropin concentration so as to maintain a polyol concentration as high as practicable. However, polyol content is limited by viscosity considerations, and the maximum polyol concentration is about 40–45% for formulations having a hormone content about 25%. Higher polyol concentrations provide a benefit in physical stability, but can result in viscosity that makes handling difficult.

Preferably the bST is an aqueous suspension of bST formulated for release in an osmotic pump as hereinafter described. Such formulations can include glycerol, monobasic and dibasic sodium phosphate buffer, Tween-80, an alkaline halide salt such as sodium chloride and/or potassium chloride, but are not limited to these ingredients, in addition to the active ingredients such as bST and the estrogenic agent.

The currently preferred formulation comprises 36.5%±1.5% for Zn-bST in a phosphate buffer, glycerols, wetting agent, salt excipient blend where the w/w/w/w proportions of phosphate buffer, glycerol, Tween-80, and KCl are 48.38/48.38/0.24/3.0 respectively. The phosphate buffer is 60:40 monobasic:dibasic sodium phosphate, and the molarity is 0.45.

The preferred composition containing an estrogenic agent comprises about 0.06% to about 3.0% 17-beta-estradiol.

According to the invention, bST is intraperitoneally released in beef cattle in the finishing stages of growth at an effective dose and rate for significantly increasing a parameter selected from the group consisting of body weight (BW), carcass weight (CW), average daily gain (ADG) or feed efficiency (FE) of the animal. By significantly increasing is preferably meant that the dose is preferably effective at $P<0.05$ which is a standard for demonstrating a beneficial effect.

The peritoneum is the serous membrane lining of the abdominal walls (parietal peritoneum) and investing the viscera (visceral peritoneum). The parietal peritoneum is the membrane which lines the abdominal and pelvic walls and the undersurface of the diaphragm. The visceral peritoneum is the membrane reflected at various places over the viscera, forming a complete covering for the stomach, spleen, liver, ascending portion of the duodenum, jejunum, ileum, transverse colon, sigmoid flexure, upper end of the rectum, uterus, and ovaries; it also partially covers the descending and transverse portions of the duodenum, the cecum, ascending and descending colon, the middle part of the rectum, the posterior wall of the bladder, and the upper portion of the vagina. The peritoneum serves to hold the viscera in position by folds, some of which form the mesenteries, which connect portions of the intestine with the posterior abdominal wall; others, the omenta, folds attached to the stomach, and still others, the ligaments of the liver, spleen, stomach, kidneys, bladder, and uterus. The space between the parietal and visceral peritoneums is the Peritoneal Cavity, which consists of the Pelvic Peritoneal Cavity below and General Peritoneal Cavity above. The General Peritoneal Cavity communicates by the Foramen of Winslow with the Cavity of the Great Omentum, which is also known as the Lesser Peritoneal Cavity. As used herein, intraperitoneal cavity includes any of the Pelvic Peritoneal Cavity, the General Peritoneal Cavity, and the Lesser Peritoneal Cavity. More preferably, the implant is inserted into the Lesser Peritoneal Cavity.

It has been established that access to the peritoneal cavity is best gained by inserting a trocar through the left paralumbar fossa. Initially, it was thought that insertion through the right paralumbar fossa would be the preferred side, as the rumen is positioned adjacent to the left paralumbar fossa. However, it was determined that the position of the kidneys and associated kidney are asymmetrically distributed toward the right side of the body and interfere with trocar access to the peritoneal cavity. For this reason access to the peritoneal cavity is more easily accomplished through the left paralumbar fossa.

The implantation is preferably accomplished using a two step procedure. In the first step, a vertical incision is made substantially through the hide alone of the left paralumbar fossa. The incision is vertical relative to the ground and preferably less than 25 mm or 20 mm in length. In the second step, a sterile non-toxic plastic tube having, for example, a 30° bevel at the tip, optionally double-beveled, and providing a substantially-non-incising puncturing tip, is inserted through the incision and into the peritoneum. Sterile implants are inserted therethrough and the tube is removed and the wound permitted to close. Further description is provided in Appendix B hereto which is incorporated herein by reference.

The bST is intraperitoneally released since it has been observed that subcutaneous daily injections or prolonged non-intraperitoneal release can result in a decrease or in a nonsignificant change in dressing percentage and have not resulted in significant increases in dressing percentage and carcass weight.

Generally, it has been found that a practical minimum rate of release for observing significant changes in body weight or carcass weight or average daily gain or feed efficiency is about 3 mg/d bST and that above about 14 mg/d bST, there is little additional improvement. For advantageous results, the intraperitoneal daily release is maintained preferably in the range of about 3 mg/d to about 14 mg/d. However, higher dosages can also be employed. More preferably the intraperitoneal daily release is maintained in the range of about 6 or 9 to about 12 mg/d.

The release is preferably continuous since daily injections or biweekly injections can cause a reduction in dressing percentage. See, e.g., Mosley et al., op. cit., and Wright et al., op. cit. However, a pulsatile intraperitoneal release enhancing dressing percent is within the scope of the invention, for example, a pulsatile release 6, 12 or more times per day so that noncarcass growth is not unduly stimulated.

The preferably continuous release can be zero-order or non-zero order provided that the release threshold is preferably maintained in the range of above about 3 mg/d to about 14 mg/d, more preferably in the range of about 9 to about 12 mg/day that is, provided that the rate of release does not fall below a value in these ranges during substantially the entire period of treatment. Preferably, also, the rate of release does not exceed values of these ranges since higher dosages of bST which are not maintained over the long term may favor increase in weight of non-carcass organs and such higher dosages may result if a prolonged continuous intraperitoneal release above the minimum is to be achieved using a non-zero release implant.

bST is released at a substantially zero-order rate of release when the rate of release is substantially independent of the amount of bST remaining in the implant. It is preferred that the release be substantially zero-order. Thus, for example, a constant rate of release is zero-order. Such a rate of release can be accomplished by an osmotic implant such as described in Appendix A attached hereto and incorporated herein by reference.

Preferably the bST administration is effected by such an implantable device capable of delivering the desired dose of bST intraperitoneally for a prolonged period of time. Preferably, as indicated, the osmotic implant is such as is described in the patent application attached hereto as Appendix A and incorporated herein by reference. Other methods of achieving a substantially zero-order rate of release can also be used, for example, a pellet of bST having an approximately constant-area release surface, or using other techniques known to those skilled in the art.

In the prior art, bST daily injection produced serum bST levels that were 400 to 700% higher than baseline for the first four hours post-injection and returned to baseline about 12 hours after injection (Enright et al., 1990 and Early et al., 1990a); whereas continuous bST delivery from a pellet has been found to produce about a 100% increase in serum bST in Holstein heifers and no detectable increase in serum bST in cross-bred steers. These data support a hypothesis, which should not be considered to limit the invention, that a less-variable more-continuous rate of delivery of bST in steers may reduce the disproportionate growth of non-carcass components by establishing an effective blood level for promoting growth of the carcass components that does not exaggerate the growth of viscera and other non-carcass components. Wagner et al., 1988, for example, used continuous delivery of bST in an oil based system at a dose of about 70 mg/d and showed a significant reduction in dressing percent. This might indicate that viscera and other non-carcass components have a broader bST dose-response window than components of the carcass. Concomitantly, the dose used by Wagner et al., 1988 was far in excess of that described as preferred herein. In a companion study Wagner et al., 1988, showed that a 960 mg dose administered about every two weeks produced about a 38-fold (3770% increase) in serum bST levels, when examined twelve days post injection of the second 960 mg dose. Such blood level changes in bST are in far excess of those required to stimulate carcass growth in steers, but potentially within the dose response of tissues associated with the non-carcass component. Accordingly, a controlled release of bST within the window for increasing dressing percentage is preferred.

In Example 4 below, intraperitoneal bST osmotic implants in feedlot cattle increased dressing percent from 61.8% for the controls up to 62.4 to 62.8% for bST treated animals. Possible explanations for this effect included 1) presence of performance enhancers (e.g., an estrogenic agent) and 2) the mode of delivery (zero-order intraperitoneal delivery). In Example 3 below, the synergistic effect of an estrogenic agent and intraperitoneal zero-order delivery of bST is demonstrated. Neither product alone caused a significant increase in dressing percent, but in combination-treated cattle there was a significant increase in dressing percent.

In a study in which cattle received an estrogenic agent and intraperitoneal bST pellets, dressing percent was not significantly affected by treatment. However, as noted above, Wagner et al., 1988 had tested a combination of an estrogenic agent and bST delivered on a continuous basis, but had found that dressing percent still dropped from 63.0% to 61.4% which advances the unexpected advantage of the current invention. It is possible that Wagner et al.'s failure to demonstrate a bST/estrogen-induced improvement in dressing percent was due to 1) the excessive bST dose (70 mg/d) and/or 2) poorly controlled bST delivery (a 960 mg 28-day dairy product injected every 14 days). Thus, the enhancement of dressing percent with an estrogenic agent and intraperitoneal bST zero-order delivery can be considered due to factors including, 1) the synergistic effects of bST and the estrogenic agent, 2) the effect of substantially zero-order osmotic bST delivery and 3) the effect of intraperitoneal delivery compared to subcutaneous delivery of bST.

Most preferably, the implant is such as described in Appendix A attached hereto and incorporated by reference. Such implants may contain about 800 mg bST and release bST at a nominal rate of about 6 to 7 mg/d. Two or more implants can be used concurrently to achieve a desired rate of release, for example, about 10 mg/d to 12 mg/d.

According to the invention, the implant, preferably providing a substantially constant release, is implanted in the intraperitoneal cavity of the bovine being treated. Implanting in the intraperitoneal cavity facilitates recovery of the implant with the non-carcass components of the bovine following slaughter. In addition, in accordance with the invention, the combination of intraperitoneal implant and substantially constant release has been found advantageous in facilitating a significant increase in dressing percent and carcass weight in bST-treated cattle.

Implantation is preferably accomplished via the left paralumbar fossa since this has been found, as indicated above, to facilitate implantation. The left paralumbar fossa is a generally triangular area on the bovine between the hip bone and the last rib and below the loin area on the left side. Tissue and hide depth here is about 0.5 to 2.0", but trocars used for implantation are generally on the order of 1 to 5 inches. The insertion depth of the trocar needs to be greater than the actual thickness of the paralumbar region due to stretching of the peritoneal lining. The only internal organs presenting a risk of injury is the rumen. Damage to the rumen can be eliminated or reduced by administering the implant to fasting or feed restricted animals. See Appendix B attached hereto and incorporated by reference. Other methods of intraperitoneal administration may also be used.

According to the invention, bST is released intraperitoneally concurrently with administration of an effective dose of an estrogenic agent. The estrogenic agent can be administered either subcutaneously or intraperitoneally.

Any estrogenic substance may be used as the estrogenic agent in the present invention. An estrogenic substance is one which when administered to a normal female animal will cause growth of the uterus and teats. However, only estrogenic substances which are suitable for administration to food animals can be put into actual use.

In actual use, the acceptable estrogens for food-producing animals are estrone and estradiol steroids such as 17-beta estradiol, estradiol benzoate, ethinylestradiol, etc. or non-steroidal compounds with estrogenic activity, such as diethylstilbesterol, hexestrol, dianestrol, zeranol, etc., and derivatives of these substances. The simple esters, such as the C1–C6 alkanoates, and the benzoates, formed on one or two of the available hydroxy groups of estradiol and zeranol, or on the one hydroxy group of estrone are useful estrogenic substances. For example, estradiol benzoate, estradiol dipropionate, estrone acetate, zeranol hexanoate, zeranol dibutyrate, 17-beta-estradiol, 17-beta-ethinyl-estradiol, can be used.

Other components which do not interfere with the desired estrogen effect, such as progesterone, cholesterol, and other binding agents, and additives may also be present.

Broadly the estrogen can be released in the range of about 5 ug/d to 500 ug/d or even higher. Preferably the estrogen is released in the range of about 15 to about 60 ug/d. Generally, the dose of estrogenic agent can advantageously be the same as that used when the estrogenic agent is administered as an anabolic agent to cattle in the finishing stage of growth to significantly increase body weight (BW) or carcass weight (CW). When the estrogenic agent is released from an intraperitoneal osmotic pump, the effective dose may be even lower, for example, in the range of 15 to 30 ug/d.

As indicated, the estrogenic agent is delivered concurrently with the intraperitoneal release of bST. The administration of the estrogenic agent can be by pellets or other means such as are well-known in the art. Preferably, the estrogenic agent is delivered intraperitoneally in the bovine using an osmotic pump, for example, the osmotic pump employed for the bST or another separate osmotic pump containing the estrogenic agent in a suitable excipient.

Preferably, the estrogenic agent is released in the bovine for a period of time generally concurrent with the period of bST delivery. However, treatment with an estrogenic agent prior to and concurrent with initial bST treatment has also been found effective.

Preferably the bST and/or estrogenic agent implant is implanted into the animals at the beginning of the finishing stage of growth. However, either the estrogenic source or the bST implant or both may also be implanted earlier and either provide a delayed initiation of bST release or a longer period of release.

In accordance with the invention, the intraperitoneal bST release is provided preferably during the entire period of the finishing stage of growth and is continued substantially until the time for slaughter of the animals. It has been previously found that the benefits of bST treatment may be adversely affected by discontinuation of bST. Hence, it is preferred that bST treatments continue at least until a time when the beneficial effects of concurrent bST and estrogen treatment will persist at slaughter, for example, until about two weeks before slaughter and most preferably that bST release be ongoing at slaughter.

The period of time during which an effective rate of intraperitoneal release must be maintained can be any period effective for significantly increasing dressing percentage and carcass weight in finishing cattle receiving an estrogenic agent. Currently, it is believed that a minimum of about 6 or even about 9–12 weeks are required. The period of bST release is preferably at least for about 12 weeks prior to slaughter and more preferably about 18 or more weeks prior to slaughter. Overall, the period of bST treatment can be from about 6 to about 24 or 30 weeks or longer preceding slaughter of the beef cattle.

To obtain full benefit of the intraperitoneal release of bST, it is preferred that the bovines be on a supplemented diet, that is, on a diet that contains more protein or carbohydrate or fat or combinations of these than is found in hay or pasturage.

The invention will be further understood and appreciated from the following Examples.

EXAMPLE 1

Weekly Subcutaneously Administered Pellets

A study was undertaken to determine the effect of 40 or 80 mg A-bST pellets administered subcutaneously weekly during a 84-day beef cattle study on 1) growth, 2) feed efficiency and 3) carcass composition.

One hundred eighty Angus X Hereford beef steers weighing approximately 350 kg (770 lbs) were used. Stocking density was 5 animals per pen. The trial consisted of 180 steers with replicates of 12 pens (60 animals) per treatment group (control, 40 mg bST/wk, and 80 mg bST/wk). The study lasted 84 days (12 weeks) exclusive of the pretreatment period. The diet for all animals, on a dry matter basis, contained 16% crude protein ("P"). Potable water was available ad libitum. Pens were randomly distributed among treatments:

| Trial | Treatment Group | Pens | Animals | Description |
|---|---|---|---|---|
| 1 | 1 | 12 | 60 | Control |
| 1 | 2 | 12 | 60 | 40 mg/wk A-bST Pellets |
| 1 | 3 | 12 | 60 | 80 mg/wk A-bST Pellets |

The animals were slaughtered for carcass analysis. The results are shown on the following Table:

TABLE

| | TREATMENT | | |
|---|---|---|---|
| Parameters | Control | 40 mg/wk bST Pellets | 80 mg/wk bST Pellets |
| Initial Body Wt (kg) | 390.3 | 390.3 | 390.3 |
| Final Body Wt (kg) | 499.5$^a$ | 495.0$^a$ | 510.4$^b$ |
| Carcass Wt. (kg) | 308.3 | 304.3 | 312.2 |
| Dressing Percent (%) | 61.7 | 61.5 | 61.2 |
| Carcass Gain Response (%) | — | No Gain | 39% |
| Non-Carcass Gain Response (%) | — | No Gain | 61% |

$^{a, b}$ - different superscripts indicate that numbers in a row are significantly different (p < .05).

It was observed that neither dressing percentage nor carcass weight were significantly increased. Further, at the higher dosage, it was observed that most of the increase in body weight due to bST treatment was allocated to the non-carcass components.

EXAMPLE 2

Weekly Subcutaneous or Intraperitoneal Pellets

A study was undertaken to determine whether the effect of 80 mg A-bST pellets during an 84-day beef cattle study was comparable when administered subcutaneously and intraperitoneally.

Two hundred seventy Angus X Hereford beef steers weighing approximately 350 kg (770 lbs) were bought and divided into three study groups. Stocking density was 5 animals per pen. Each study group consisted of replicates of 6 pens (30 animals) per treatment group (control, 40 mgbST/wk subcutaneous pellet, and 80 mgbST/wk intraperitoneal pellet). The study lasted 84 days exclusive of the pretreatment period. The diet for all animals, on a dry matter basis, contained 16% crude protein. Potable water was available ad libitum. Pens were randomly distributed among the treatments:

| Trial | Treatment | Pens | Animals | Description |
|---|---|---|---|---|
| 2 | 1 | 12 | 30 | Control |
| 2 | 2 | 12 | 30 | 80 mg/wk A-BST Subcutaneous (SQ) Pellet |
| 2 | 3 | 12 | 30 | 80 mg/wk A-BST (IP) Intraperitoneal Pellet |
| 3 | 1 | 12 | 30 | Control |

-continued

| Trial | Treatment | Pens | Animals | Description |
|---|---|---|---|---|
| | 2 | 12 | 30 | 80 mg/wk bST SQ Pellet |
| | 3 | 12 | 30 | 80 mg/wk bST IP Pellet |
| | 1 | 12 | 30 | Control |
| | 2 | 12 | 30 | 80 mg/wk A-BST SQ Pellet |
| | 3 | 12 | 30 | 80 mg/wk A-BST IP Pellet |

The animals were slaughtered for carcass analysis. The results are shown in the following Tables:

TABLE

| | TREATMENT | | |
|---|---|---|---|
| Parameters | Control | 80 mg/wk SQ bST Pellets | 80 mg/wk IP bST Pellets |
| Initial Body Wt (kg) | 395.1 | 395.0 | 399.7 |
| Final Body Wt (kg) | 493.7$^a$ | 499.5$^a$ | 507.8$^b$ |
| Carcass Wt. (kg) | 304.2$^a$ | 304.2$^a$ | 311.2$^b$ |
| Dressing Percent (%) | 61.6$^a$ | 60.8$^b$ | 61.2$^{ab}$ |
| Carcass Gain Response (%) | — | 0% | 61% |
| Non-Carcass Gain Response (%) | — | 100% | 39% |

$^{a, b}$ - different superscripts indicate that numbers in a row are significantly different (p < .05).

It can be seen that, while the dressing percentage of subcutaneously-treated cattle was significantly decreased relative to the control, the dressing percentage of intraperitoneally-treated cattle was not significantly changed relative to the control.

EXAMPLE 3

Combination of Intraperitoneal bST Osmotic Pump and Estrogen Pellets

A study was undertaken to determine the effects of intraperitoneal release of bST, of subcutaneous estrogen pellets, or of the combined effects of the two.

Two hundred fifty-six cross-bred large frame steers weighing approximately 430 kg (966 lb) were assigned to a control group and three treatment groups and implanted with intraperitoneal bST pumps or/and subcutaneous estrogen pellets. The bST formulation used was a 35% Zn$^-$ bST load in a phosphate buffer, glycerol, and Tween-80. The w/w/w % proportions respectively were 48.38/48.38/0.24. The phosphate buffer was 60:40 monobasic:dibasic sodium phosphate at 1.0M. The time of release of both bST and estrogen was 87 days prior to slaughter. The results are shown in the following Table.

TABLE

| | TREATMENT | | | |
|---|---|---|---|---|
| Parameters | Control | 12 mg/d bST 0 Estrogen | 0 bST/200 ug/d Estrogen | 12 mg/d bST//200 ug/d Estrogen |
| Initial Body Wt (kg) | 430.3 | 430.3 | 430.3 | 430.3 |
| Final Body Wt (kg) | 544.9$^a$ | 552.2$^b$ | 567.1$^c$ | 576.4$^d$ |
| Carcass Wt (kg) | 334.2$^a$ | 340.3$^b$ | 349.3$^c$ | 359.7$^d$ |
| Dressing Percent (%) | 61.3$^a$ | 61.6$^a$ | 61.6$^a$ | 62.4$^b$ |
| Carcass Gain Response (%) | N/A | 84% | 68% | 112% |
| Non-Carcass Gain Response (%) | N/A | 16% | 32% | −12% |

$^{a,b}$ different superscripts indicate that number in a row are significantly different (P < .05)

These results indicated that a significant improvement in dressing percentage and carcass weight were achieved by intraperitoneal osmotic pump release of bST concurrent with estrogen treatment.

EXAMPLE 4

Combination of Intraperitoneal bST Osmotic Pump and Estrogen Pellet

A study was undertaken to determine performance of intraperitoneal osmotic pumps in finishing cattle concurrently being administered estrogen. Six hundred seventy-two cross-bred large frame cattle weighing approximately 412 kg were bought and assigned to a control group and six treatment groups of 96 cattle each. The cattle were implanted with intraperitoneal osmotic pumps capable of delivering 6, 12, 15 or 18 mg bST per day during an 84-day period ending with slaughter. The cattle received subcutaneous estrogen pellets during a 126-day period ending with slaughter. The estrogen release is estimated at about 200 ug/d. The results are shown in the following table.

TABLE

| | | TREATMENT | | | | | |
|---|---|---|---|---|---|---|---|
| | | 30% bST Load | 40% bST Load | Load | 45% bST Load | | |
| Parameters | Control | 6 mg/d | 12 mg/d | 15 mg/d | 6 mg/d | 12 mg/d | 18 mg/d |
| Initial Body Wt (kg) | 411.9 | 411.9 | 411.9 | 411.9 | 411.9 | 411.9 | 411.9 |
| Final Body Wt (kg) | 555.1$^a$ | 565.6$^{bc}$ | 568.7$^{bc}$ | 569.6$^c$ | 561.8$^b$ | 563.5$^{bc}$ | 566.5$^{bc}$ |
| Carcass Wt (kg) | 343.0$^a$ | 353.1$^{bc}$ | 357.2$^d$ | 355.4$^{cd}$ | 350.8$^b$ | 351.3$^b$ | 353.8$^{bcd}$ |
| Dressing Percent (%) | 61.8$^a$ | 62.4$^b$ | 62.8$^b$ | 62.4$^b$ | 62.4$^b$ | 62.4$^b$ | 62.5$^b$ |
| Carcass Response (%) | — | 96% | 104% | 86% | 116% | 99% | 95% |
| Non-Carcass Response (%) | — | 4% | −9% | 14% | −16% | 1% | 5% |

$^{a, b}$ - different superscripts indicate that numbers in a row are significantly different ($p < .05$).

The results of Examples 3 and 4 indicate that concurrent intraperitoneal treatment of finishing beef cattle with intraperitoneal bST and estradiol significantly increase dressing percentage and carcass weight and furthermore allocate most of the increased weight to the carcass components.

We claim:

1. A method of preparing beef cattle for slaughter comprising:
   inserting into the intraperitoneal cavity of a bovine in the finishing stage of growth a source of bovine somatotropin effective for prolonged release;
   the bovine being adminstered an estrogenic agent at a rate effective for increasing one of the parameters selected from the group consisting of average daily gain and carcass weight and body weight of cattle;
   the source of sonatotropin being effective for approximately zero order delivery and releasing intraperitoneally in the bovine a dose of bovine sonatotropin sustained in a range effective for increasing average daily gain of cattle;
   continuing the somatotropin release in the bovine for a period of time greater than about 9 weeks and continuing substantially until slaughter of the bovine;
   the bovine maintaining an average daily gain greater than 1 kilogram per day during said period.

2. The method of claim 1 wherein:
   the source of somatotropin is effective for delivery of a dose of bovine somatotropin in the range of about 3 to about 14 milligrams per day.

3. The method of claim 1 wherein:
   the source of somatotropin is effective for approximately zero order delivery of a dose of bovine somatotropin in the range of about 6 to about 14 milligrams per day.

4. The method of claim 1 wherein:
   the source of somatotropin is effective for approximately zero order delivery of a dose of bovine somatotropin in the range of about 9 to about 14 milligrams per day.

5. The method of claim 1 wherein:
   the period of somatotropin release is continued for a period greater than about 12 weeks and continuing substantially until slaughter of the bovine.

6. The method of claim 1 wherein:
   the period of somatotropin release is continued for a period greater than about 18 weeks and continuing substantially until slaughter of the bovine.

7. The method of claim 1 wherein
   the period of somatotropin release is continued for a period from about 12 weeks to about 30 weeks ending substantially with slaughter of the bovine.

8. The method of claim 1 wherein:
   the source of somatotropin is effective for substantially zero order intraperitoneal release during a prolonged period of time of up to about 30 weeks.

9. The method of claim 1 wherein:
   the bovine is administered an estrogenic agent at a dosage in the range of about 5 to about 500 micrograms per day.

10. The method claim 1 wherein:
    the period of time comprises a period when the average weight of the cattle is equal to or greater than about 320 kg (700 pounds).

11. The method of claim 1 wherein:
    the period of time comprises a period when the cattle are experiencing an average daily gain equal to or greater than 1.5 kilograms per day.

12. The method of claim 1 wherein:
    the period of time commences at the time of transfer of a bovine to a feedlot and continues until slaughter.

13. The method of claim 1 wherein:
    the source of bovine somatotropin further comprises the estrogenic agent.

14. A method of preparing beef cattle for slaughter comprising:
    inserting into the peritoneal space of cattle in the finishing stage of growth a source of bovine somatotropin effective for prolonged release, the source of somatotropin being effective for approximately zero order delivery;

the cattle further being treated with an estrogenic agent at a dose effective for increasing the body weight or carcass weight or both of bovines;

releasing bovine somatotropin in the intraperitoneal space at a dose effective for increasing a parameter selected from the group consisting of body weight, carcass weight, feed conversion efficiency and average daily gain of bovines; and the bovine somatotropin and the estrogenic agent being effective for significantly increasing the dressing percentage and carcass weight of bovines relative to non-bovine-somatotropin- non-estradiol-treated cattle.

* * * * *